(12) United States Patent
Bischoff et al.

(10) Patent No.: US 9,237,965 B2
(45) Date of Patent: Jan. 19, 2016

(54) RE-TREATMENT FOR OPHTHALMIC CORRECTION OF REFRACTION

(71) Applicant: CARL ZEISS MEDITEC AG, Jena (DE)

(72) Inventors: Mark Bischoff, Jena (DE); Dirk Muehlhoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/135,695

(22) Filed: Dec. 20, 2013

(65) Prior Publication Data

US 2014/0107633 A1   Apr. 17, 2014

Related U.S. Application Data

(62) Division of application No. 12/109,921, filed on Apr. 25, 2008, now Pat. No. 8,623,038.

(60) Provisional application No. 60/914,179, filed on Apr. 26, 2007.

(51) Int. Cl.
  *A61F 2/00* (2006.01)
  *A61F 9/008* (2006.01)
  *A61K 9/00* (2006.01)

(52) U.S. Cl.
  CPC .............. *A61F 9/008* (2013.01); *A61F 9/00827* (2013.01); *A61F 9/00836* (2013.01); *A61F 2009/0088* (2013.01); *A61F 2009/00872* (2013.01); *A61K 9/0048* (2013.01)

(58) Field of Classification Search
  None
  See application file for complete search history.

(56) References Cited

U.S. PATENT DOCUMENTS

| 5,656,186 A | 8/1997 | Mourou et al. |
| 5,993,438 A | 11/1999 | Juhasz et al. |
| 6,364,873 B1 | 4/2002 | McMillen et al. |
| 2002/0154270 A1 | 10/2002 | Halpern et al. |
| 2003/0078753 A1 | 4/2003 | Campin et al. |
| 2007/0027438 A1 | 2/2007 | Loesel et al. |
| 2007/0173793 A1 | 7/2007 | Rathjen |
| 2008/0058781 A1 | 3/2008 | Langeweyde et al. |
| 2008/0319428 A1 | 12/2008 | Wiechmann et al. |
| 2009/0281529 A1 | 11/2009 | Carriazo |

FOREIGN PATENT DOCUMENTS

| EP | 1 719 483 A1 | 11/2006 |
| WO | WO 00/27324 A1 | 5/2000 |
| WO | WO 2006/087180 A2 | 8/2006 |
| WO | WO 2007/012924 A1 | 2/2007 |

OTHER PUBLICATIONS

Montague, MD, Artis A., et al., "CustomVue laser in situ keratomileusis treatment after previous keratorefractive surgery," *J. Cataract Refract Surg*, vol. 32, pp. 795-798 (May 2006).
*Intralase Product Leaflet*, Essential Technology for Biomechanical Stability, Intralase Corp., 6 pgs. (2006).

*Primary Examiner* — Susan Tran
(74) *Attorney, Agent, or Firm* — Christensen Fonder P.A.

(57) ABSTRACT

A planning device generating control data for a treatment apparatus for refraction-correcting ophthalmic surgery is provided, said apparatus using a laser device to separate a corneal volume, which is to be removed for correction, from the surrounding cornea by at least one cut surface in the cornea of an eye, said planning device comprising an interface for receiving corneal data including information on pre-operative cuts which were generated in a previous ophthalmic operation, and computing means for defining a corneal cut surface which confines the corneal volume to be removed, said computing means defining the corneal cut surface on the basis of the corneal data and generating a control dataset for the corneal cut surface for control of the laser device.

6 Claims, 4 Drawing Sheets

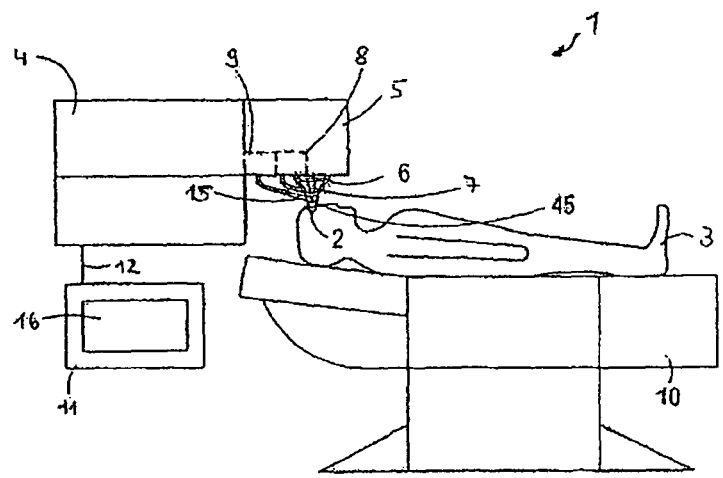
Fig. 1
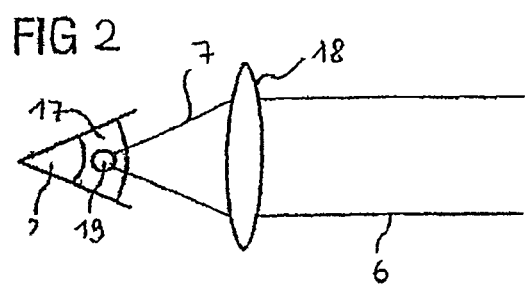
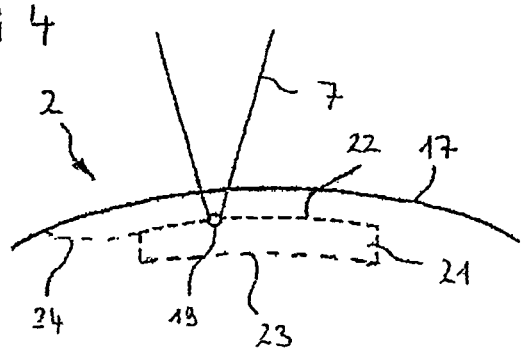

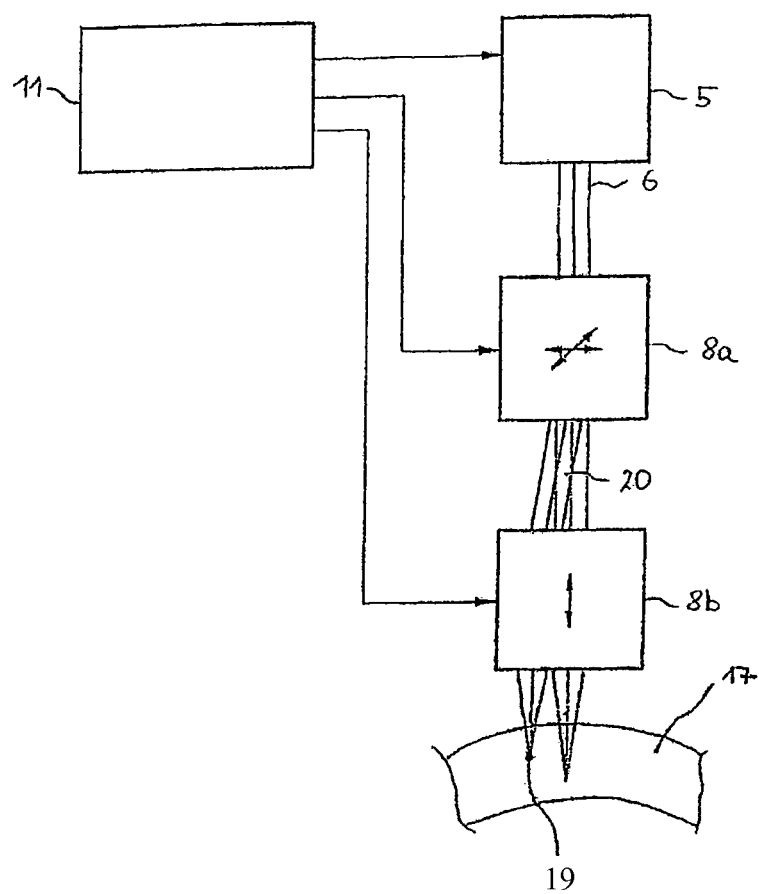

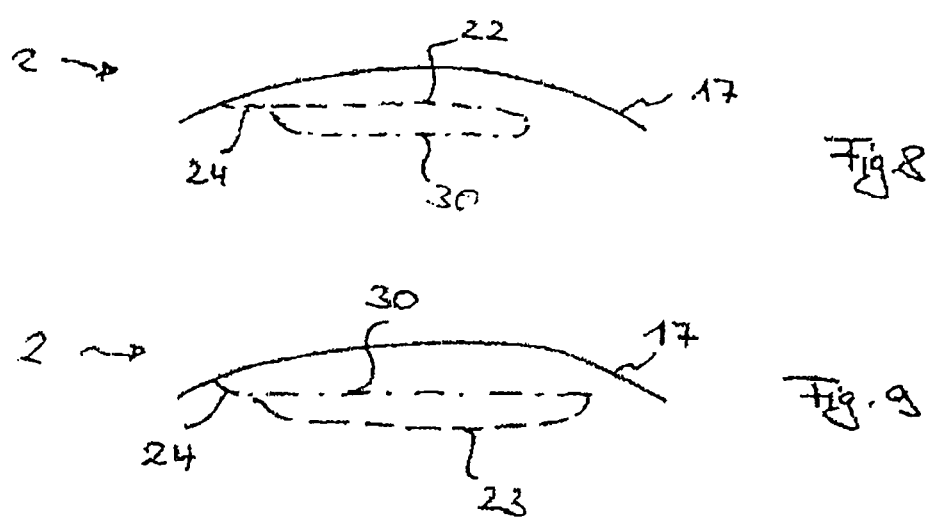

RE-TREATMENT FOR OPHTHALMIC CORRECTION OF REFRACTION

CROSS-REFERENCES TO RELATED APPLICATIONS

The present application is a divisional of Ser. No. 12/109,921, filed Apr. 25, 2008, now U.S. Pat. No. 8,623,038, issued Jan. 7, 2014, which claims the benefit of U.S. Provisional Application No. 60/914,179, filed Apr. 26, 2007, all of which are incorporated herein in their entirety by reference.

BACKGROUND OF THE INVENTION

1. Field of the Invention

The invention relates to a planning device generating control data for a treatment apparatus for refraction-correcting ophthalmic surgery, said apparatus using a laser device to separate a corneal volume, which is to be removed for correction, from the surrounding cornea by at least one cut surface in the cornea. The invention further relates to a treatment apparatus for refraction-correcting ophthalmic surgery, said apparatus comprising a planning device of the aforementioned type.

The invention further relates to a method of generating control data for a treatment apparatus for refraction-correcting ophthalmic surgery, which apparatus uses a laser device to separate a corneal volume, which is to be removed for correction, from the surrounding cornea by at least one cut surface in the cornea.

Finally, the invention also relates to a method for refraction-correcting ophthalmic surgery, wherein a corneal volume, which is to be removed for correction, is separated from the surrounding cornea by at least one cut surface formed in the cornea by a treatment apparatus comprising a laser device.

2. Background

In the prior art, the most diverse treatment methods aiming to correct refraction of the human eye are known. The aim of said surgical methods is to selectively modify the cornea so as to influence the refraction of light. Various surgical methods are employed for this purpose. The most common method is presently the so-called laser in situ keratomileusis, also abbreviated as LASIK, wherein a corneal lamella is first detached on one side and folded aside. The detachment of said lamella can also be effected using a mechanical microkeratome or a so-called laser keratome as distributed, for example, by Intralase Corp., Irvine, USA. Once the lamella has been detached and folded aside, the LASIK operation provides for the use of an excimer laser which ablates the corneal tissue thus exposed under the lamella. After a volume located beneath the corneal surface has been evaporated in this manner, the corneal lamella is folded back in its original place.

The application of a laser keratome for exposing the lamella is advantageous as compared to a mechanical knife, because it reduces the risk of infection while improving the cut quality. In particular, the lamella may be produced with a much more constant thickness if laser radiation is used. Also, the cut is generally smoother, which reduces the risk of subsequent optical impediments by this boundary surface which still remains after surgery. However, this method has the disadvantage of requiring the use of two different treatment apparatuses, namely the laser keratome for exposing the lamella, on the one hand, and the laser evaporating the corneal tissue, on the other hand.

These disadvantages are overcome by a method recently implemented by Carl Zeiss Meditec AG and abbreviated by the term FLEX. In this method, a femtosecond laser is used to form such a cut geometry in the cornea that a corneal volume (a so-called lenticle) is separated within the cornea. This corneal volume is then removed manually by the surgeon. The advantage of this method is, on the one hand, that the cut quality is further improved by the use of the femtosecond laser. On the other hand, only one treatment apparatus is required because the excimer laser is no longer employed.

When generating cut surfaces in the cornea by laser radiation, the optical radiation effect is usually taken advantage of to generate an optical breakthrough. It is also known to introduce individual pulses, whose energy is below a threshold value for an optical breakthrough, into the tissue or the material in a superimposed manner such that a separation of material or tissue is also achieved thereby. This concept of cut generation in the corneal tissue allows a great variety of cuts.

The result of treatment remaining in these described laser-surgical methods is a cut in the cornea, and although it is no longer visible to the naked eye after a short time, it never heals due to the particular nature of the cornea, because the cornea is "dead" tissue in this respect. Due to the cut, the parts of tissue above the cut are no longer fixedly connected to the parts of tissue below the cut.

However, a need for re-treatments may arise, namely if either the result of the previous operation is not yet satisfactory in terms of the correction of refraction, or if the previous operation was not sufficiently completed for any reason (e.g. due to termination of the operation).

In the case of an insufficient refractive correction, it is known for the excimer laser-based LASIK operation to lift off the corneal lamella again and to remove additional corneal tissue for re-treatment.

However, this approach is impractical for the FLEX method, because it would not allow a re-treatment to be carried out by the same device as for the previous operation, so that it would be mandatory to keep an extra device ready merely for re-treatments.

For terminated laser-based FLEX operations, in fact, no useful or safe solution is known at all.

SUMMARY OF THE INVENTION

Therefore, it is an object of the invention to provide a planning device for generating control data, a treatment apparatus for refraction-correcting ophthalmic surgery, as well as a method of generating control data for such treatment apparatus or a method for refraction-correcting ophthalmic surgery, which simply enables re-treatment without ablation of corneal tissue or continuation of a terminated treatment, respectively.

According to the invention, this object is achieved by a planning device of the above-mentioned type. The planning device comprises an interface for receiving corneal data including information on pre-operative cuts which were generated in a previous ophthalmic operation and computing means for defining a corneal cut surface. The computing means confines the corneal volume to be removed and defines the corneal cut surface on the basis of the corneal data, then generates a corneal cut surface control dataset for control of the laser device.

The object is further achieved by a treatment apparatus for refraction-correcting ophthalmic surgery. This treatment apparatus comprises an interface, a laser device, and a planning device. The interface supplies the corneal data including information on pre-operative cuts which were generated in a previous ophthalmic surgery. The laser device separates a corneal volume, which is to be removed, from the surrounding cornea by at least one cut surface formed in the cornea by laser radiation according to control data. The planning device may be of the type just mentioned, which generates the control data.

The object is finally also achieved by a method of generating control data according to the above-mentioned type, said method comprising: accessing corneal data, which include information on pre-operative cuts generated in a previous ophthalmic operation; defining a corneal cut surface, which confines the corneal volume to be removed, on the basis of the corneal data, and generating a control dataset for the corneal cut surface for control of the laser device.

Finally, the object is also achieved by a method of refraction-correcting ophthalmic surgery, which comprises: accessing corneal data, which include information on pre-operative cuts generated in a previous ophthalmic operation; defining a corneal cut surface, which confines the corneal volume to be removed, on the basis of the corneal data, and generating a control dataset for the corneal cut surface; transmitting the control data to the treatment apparatus, and generating the cut surfaces by control of the laser device using the control dataset.

The object is further achieved by the use of a treatment apparatus for a refraction-correcting ophthalmic operation, said treatment apparatus comprising a laser device, which forms a cut surface in cornea by pulsed laser radiation in order to isolate in the cornea a corneal volume which is to be removed for correction, said ophthalmic operation being effected as a re-treatment of a previous operation which left cuts in the cornea.

Because the inventors realized that such an apparatus can be applied in a surprisingly unproblematic manner to cases in which cuts have already been made pre-operatively in the cornea, this concept provides for a re-treatment using an apparatus known for the FLEX method.

Thus, the invention quite generally provides for generating at least one additional cut surface in the cornea, which cut surface isolates a corneal volume whose removal results in the desired refractive correction. In the state of the art, such corneal volume is also referred to as a lenticle, because it is lenticular in most cases.

By taking into consideration the pre-operative cuts, i.e., those cuts already existing as a result of the previous operation, a re-treatment can now be carried out both in cases where a residual correction of refraction is still required and in cases where the previous operation was not duly completed, i.e., terminated. Particularly in the latter cases, there has been no suitable means whatsoever in the prior art to achieve a correction of refraction by an ophthalmic method.

A re-treatment is advantageously carried out such that the corneal cut surface defined by the planning device, by the planning method, the corneal cut surface generated by the treatment apparatus, or the treatment method does not intersect the pre-operative cuts. This has the advantage of avoiding any undesired isolation of volumes in the cornea which are possibly removed from the cornea along with the removal of the actually intended volume and lead to an unpredictable alteration of the corneal surface. Further, this also avoids undesired weakening when folding aside the lamella isolated during re-treatment or undesired folding aside of further parts of the cornea, in a manner not intended, which folding could occur due to an insufficiently considered pre-operative cut.

Such negative occurrences during re-treatment can be avoided in a particularly reliable manner if the computing means of the planning device or the corresponding planning method, respectively, define the cut surface in the cornea such that the corneal volume to be removed is located completely posterior to the pre-operative cuts generated, completely anterior to the pre-operative cuts, or encloses the pre-operatively generated cuts.

The first or second variant are particularly suitable in cases where the previous operation went according to plan, but a residual eyesight defect still has to be corrected. The third variant is suitable in cases where the previous operation—for whatever reasons—was terminated, because the remaining pre-operative cuts, whose position may possibly not be determined with absolute precision, are removed from the cornea when removing the corneal volume isolated by the re-treatment.

On the other hand, if the position of the pre-operative cuts is, or can be determined, with sufficient precision, an alternative of the invention allows the corneal cut surface to be defined as a continuation of the pre-operative cuts.

Because the existing pre-operative cuts have to be taken into consideration, the planning of the corneal cut surface is of particular importance in the case of a re-treatment. This planning is facilitated for the surgeon if a display device for visual representation of the cornea and of the existing pre-operative cuts, preferably in a superimposed representation, is provided.

It is a particular advantage that specific data can be used for planning and execution of the re-treatment. These may be data of the previous operation, which are stored in the apparatus; diagnostic data of the eye to be treated, which were acquired after the previous operation and prior to the re-treatment; or data of the eye to be treated, which were acquired intra-operatively, i.e. during re-treatment. Advantageously, such corneal data can be generated on the basis of a measurement of the eye and can be supplied to the planning device, in which case a measurement device is used which optionally comprises one or more of the following devices: autorefractor, refractometer, keratometer, aberrometer, wavefront measurement device, OCT, confocal corneal microscopy, Scheimpflug camera, and topographic measurement.

If a re-treatment is carried out due to a residual need for correction, i.e. if the previous operation was completed according to plan, a particularly important detail is, of course, the eyesight defect to be corrected and/or the thickness and/or diameter of a pre-operatively generated corneal lamella which can be folded aside.

A re-treatment can be carried out more easily or precisely when accurate knowledge of the pre-operatively existing cut is available. Therefore, it is advantageous, quite generally and independently of the realization of the re-treatment, if a laser-surgical treatment apparatus for refractive ophthalmic surgery comprises a device which logs the progress of the generated cuts during an operation. If the treatment apparatus uses pulsed laser radiation, said logging may include the position and the energy of each laser radiation pulse focused into the cornea. The relative position of the cornea (or the eye, respectively) and of the apparatus is also logged. Such logging is unknown in the prior art. In fact, such logging goes far beyond the usual extent of available information which comprises information on the patient, the need for correction of refraction and, at best, the cut surface geometry used. Accordingly, the data storage volume is advantageous, even though considerable in volume, when a re-treatment is required, especially if the previous operation was not completed. If so, simple and precise continuation of the terminated cut surface generation is then possible.

For re-treatment, the invention provides for the defined or used cut surfaces to be geometrically arranged such that either no intersection occurs at all with the pre-operative, already existing cut or that this cut is suitably supplemented or continued.

Several cases are distinguished. In the case of a subsequent refractive correction by which the previous method is duly completed, the additional cuts can be arranged such that they are located less deeply below the corneal surface than the pre-operatively existing cut which was generated to fold the corneal lamella aside. As an alternative, it is possible to arrange the corneal cut surface at a greater depth than the pre-operatively existing cut. The lenticle to be removed is then removed from a corneal region which is located below the pre-operatively generated corneal lamella. By contrast, the lenticle may be located within the corneal lamella in the first-mentioned case.

These variants, as with the variant in which the corneal volume encloses the pre-operatively existing cut, are based on the concept that the corneal volume to be removed, usually in the shape of a lenticle, is generated without re-using the pre-operative cuts, e.g. by a separate flap cut as well as a separate lenticle cut.

As an alternative, it is possible to use the already existing pre-operative cut and to define the corneal cut surface such that the corneal cut surfaces supplement or utilize the pre-operative cut when isolating the corneal volume to be removed by re-treatment. The lenticle is then limited by the pre-operatively existing cut as well as by the defined corneal cut surface. Cut surfaces are thus generated more quickly. However, this protocol requires precise knowledge of the pre-operative cut. Supplementing may accordingly be effected above the pre-operative cut, i.e. through the corneal lamella or below the pre-operative cut, i.e. towards the inner surface of the cornea.

In the case of a re-treatment preceded by a previous operation that was not completed, there is always the problem that, depending on how the pre-operative cut was generated, there may exist only incomplete cut surfaces. For example, a lenticle cut intended to posteriorly limit the corneal volume that should have been removed by the previous operation may have been carried out completely or partially. However, there may possibly be also a partial or even nearly complete flap cut which was intended to limit the lenticle anteriorly. There may also be a case in which the peripheral cut, which allows the corneal lamella to be folded aside, is the only cut which has not been completed. In each case, it is often adequate to continue these cuts if the pre-operatively generated cuts are precisely known. The continuation may also be such that the cut surface includes part of the pre-operative cut already generated, i.e. generating the re-treatment cut surface is begun in a region in which a pre-operative cut is already expected. An overlap ensures continuous separation of tissue by the combined effect of the pre-operative cut and of the cut surface generated during re-treatment. If it is not desired to continue the pre-operative cuts, e.g. because their positions are not sufficiently precisely known or the quality of these cuts is not satisfactory, the cut surface for isolation of the corneal volume to be removed is often conveniently defined such that it is either completely anterior to the pre-operative cuts, completely posterior to the pre-operative cuts, or confines the pre-operative cuts in the corneal volume to be removed.

As the discussion of the re-treatment shows, it may be important to determine the position of the pre-operative cut in order to position the corneal cut surfaces as exactly as possible. Alternatively, 1. The position of the pre-operative cut is measured by diagnostic methods prior to carrying out the re-treatment. The diagnostic methods may comprise confocal microscopy of the cornea, optical coherence tomography, or the use of a slit lamp with a measurement camera connected thereto.

2. Position data of the pre-operative cuts can be derived from internal data from the apparatus by which the previous operation was conducted. Thus, in planning the re-treatment, input data used to plan the previous operation and/or data acquired during execution of the previous operation may be used. Examples of data which can be acquired during execution of the previous operation include: data from an intraoperative measurement of the residual stroma thickness, data concerning the time at which the operation was terminated and/or data concerning the real position of the cuts generated by the previous operation.

3. Position data concerning the pre-operatively generated cuts during the re-treatment can also be determined by a measurement system provided in the apparatus for the re-treatment. Stated otherwise, the position data concerning the pre-operatively existing cuts may be intraoperatively determined. Such a measurement system may use a confocal sensor or optical principles of coherence tomography. It is also possible to execute a test cut using the treatment apparatus and to derive the position of the pre-operatively existing cut from the data of an observation camera.

Describing the position of the pre-operatively existing cut generally requires the complete indication of the function $z(x,y)$ for all pairs of coordinates $(x,y)$ of the cut area. However, a considerable reduction of parameters is possible, e.g. for a circular flap of homogeneous thickness. In this case, it is sufficient to determine flap thickness, flap diameter, and the position of the flap's center.

During execution of a laser-surgical operation carried out using pulsed laser radiation, the position of the laser focus follows a previously computed trajectory $\bar{s}(t):=R^1 \to R^3$, with $t\in I=[0,T]\subset R$, for the purpose of generating a two-dimensional cut surface $S:=R^2 \to R^3$. R is the quantity of real numbers and $R^n$ is the $n^{th}$ dimension Euclidian vector space.

Individual partial cut surfaces $S_j \subset S$ are sequentially represented by $\bar{s}(t)$, i.e. for each partial cut surface $S_j$, there is exactly one interval $I_j=[t_1,t_2]_j$ from which the trajectory $\bar{s}(t)$ of $S_j$ comes. Due to the strict sequencing of the cut surfaces $S_j$ in the trajectory $\bar{s}(t)$, the individual intervals are disjoint, i.e.

$$\exists! I_j \subset I | \forall t\in I_j | \bar{s}(t)\in S_j \wedge \forall i\neq j | I_i \cap I_j = \emptyset$$

holds true.

The trajectory $\bar{s}(t)$ can be computed, for a specific laser therapy, together with the corresponding set of disjoint intervals $I_j$. During laser therapy, the parameter t passes through the interval $I=[0,T]$. The therapy is complete as soon as $t=T$ or at least $$\forall k \in \bigcup_j I_j \,|\, t \geq k.$$

If the therapy is terminated at $t=t_{int}$, the intervals $I_j$ determine at which cut surface the termination took place, or how far this cut surface has been completed. A partial cut surface $S_j$ is complete when $\forall k \in I_j | k \leq t_{int}$ holds true. Thus, in order to determine the location where the therapy was terminated, it is sufficient to determine the time at which it was terminated. It is possible here to determine the time within a certain tolerance, i.e. for example at a resolution of 1% of T.

Determining the termination time makes logging easier and safer. Therefore, it is advantageous to simplify logging such that it does not involve logging the position of each laser radiation pulse emitted into the cornea, but merely the logging of parameters of the emission of laser radiation pulses (e.g. frequency of the pulses), of focus deflection (e.g. deflection speed), as well as indicating the exact time of any termination of the operation and cut geometry data.

It is not decisive for the invention how the pre-operative cuts were generated. Thus, in principle, they may also have been generated using a mechanical microkeratome or the like.

It will be appreciated that the above-mentioned features and those yet to be explained below can be employed not only in the combinations indicated, but also in other combinations or alone, without departing from the scope of the present invention.

BRIEF DESCRIPTION OF THE DRAWINGS

The invention will be explained in more detail below with reference to the enclosed drawings, which also disclose features essential to the invention and wherein:

FIG. 1 shows a schematic representation of a treatment apparatus comprising a planning device for a re-treatment in connection with ophthalmic correction of refraction;

FIG. 2 shows a schematic representation of the effect of the laser radiation used in the treatment apparatus of FIG. 1;

FIG. 3 shows a further schematic representation of the treatment apparatus of FIG. 1 with respect to the introduction of the laser radiation;

FIG. 4 shows a schematic sectional view of the cornea, illustrating the removal of the corneal volume in connection with the ophthalmic correction of refraction;

FIG. 8 shows a further schematic sectional view of the cornea in connection with the ophthalmic correction of refraction in a re-treatment for continuation of a terminated previous operation by continuing the existing cut surface; and FIG. 9 shows a further schematic sectional view of the cornea in connection with the ophthalmic correction of refraction in a re-treatment for correction of a residual eyesight defect, using the existing cut surface.

DETAILED DESCRIPTION

Figure 5:
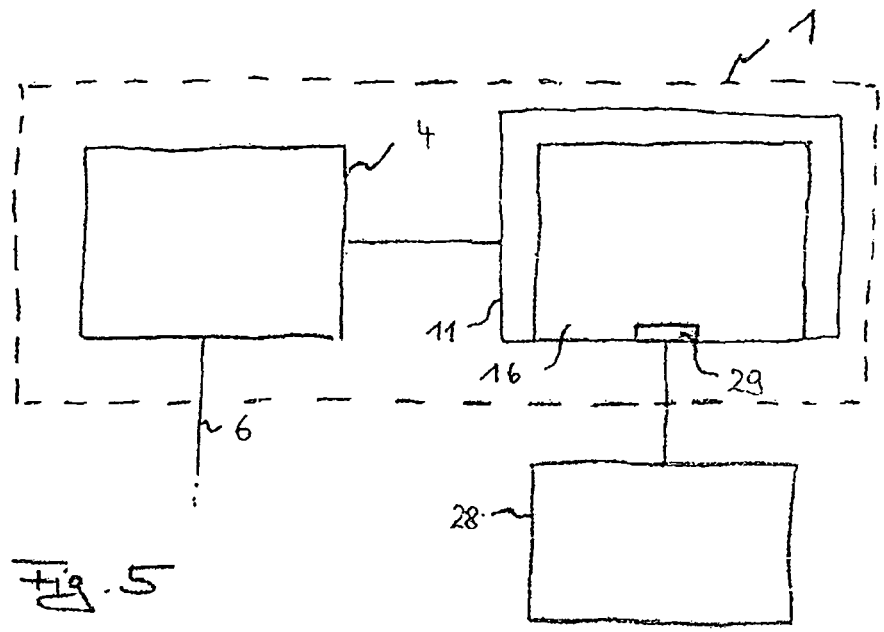
FIG. 5 shows a schematic representation relating to the construction of the treatment apparatus of FIG. 1 with particular reference to the planning device present.

A treatment apparatus for ophthalmic correction of refraction is shown in FIG. 1 and generally indicated at 1. The treatment apparatus 1 is provided for re-treating correction of refraction to the eye 2 of a patient 3. For this purpose, the treatment apparatus 1 comprises a laser device 4, which emits a laser beam 6 from a laser source 5, said beam being directed as a focused beam 7 into the eye 2 or into the cornea. The laser beam 6 is preferably a pulsed laser beam having a wavelength of between 400 nanometers and 10 micrometers. Further, the pulse duration of the laser beam 6 is in the range of between 1 femtosecond and 10 picoseconds, with pulse repetition frequencies of from 1 to 1000 kilohertz and pulse energies of between 0.01 microjoules and 0.01 millijoules being possible. Thus, the treatment apparatus 1 generates a cut surface in the cornea of the eye 2 by deflection of the pulsed laser radiation. For this purpose, the laser device 4 or its laser source 5, respectively, also includes a scanner 8 as well as a radiation intensity modulator 9.

The patient 3 is lying on a table 10, which is shiftable in three spatial directions in order to align the position of the eye 2 with the incidence of the laser beam 6. In a preferred construction, the table 10 is shiftable by a motor drive.

Control may be effected, in particular, by a control device 11, which generally controls the operation of the treatment apparatus 1 and is connected to the treatment apparatus via suitable data links, for example connecting lines 12, for this purpose. This communication may, of course, be effected also via other paths, e.g. by light guides or by radio. The control device 11 performs the corresponding settings, time control of the treatment apparatus 1, in particular of the laser device 4, and thus performs corresponding functions of the treatment apparatus 1.

The treatment apparatus 1 further comprises a fixing device 15 which positionally fixes the cornea of the eye 2 with respect to the laser device 4. This fixing device 15 may comprise a known contact glass 45 with which the cornea is placed in contact by a vacuum and which imparts a desired geometrical shape to the cornea. The person skilled in the art is familiar with such contact glasses from the prior art, for example from DE 102005040338 A1. The disclosure of this document is fully incorporated herein by reference as far as the description of a construction of the contact glass 45 usable for the treatment apparatus 1 is concerned.

The control device 11 of the treatment apparatus 1 further comprises a planning device 16, which will be explained in more detail below.

FIG. 2 schematically shows the effect of the incident laser beam 6. The laser beam 6 is focused and is incident in the cornea 17 of the eye 2 as the focused laser beam 7. Schematically indicated optics 18 are provided for focusing. They effect a focus in the cornea 17, in which focus the laser radiation energy density is so high that, in combination with the pulse duration of the pulsed laser radiation 6, a non-linear effect appears in the cornea 17. For example, each pulse of the pulsed laser radiation 6 in the focus 19 may produce an optical breakthrough in the cornea 17, which in turn initiates a plasma bubble indicated only schematically in FIG. 2. When the plasma bubble forms, the tissue layer separation comprises an area larger than the focus 19, although the conditions for producing the optical breakthrough are achieved only in the focus 19. In order for an optical breakthrough to be generated by each laser pulse, the energy density, i.e. the fluence of the laser radiation, must be above a certain pulse duration-dependent threshold value. This connection is known to the person skilled in the art, for example, from DE 69500997 T2. Alternatively, a tissue-separating effect can also be achieved by pulsed laser radiation in that several laser beam radiation pulses are emitted in a region where the focus spots overlap. In this case, several laser radiation pulses cooperate to achieve a tissue-separating effect.

However, the type of tissue separation used by the treatment apparatus 1 is not really relevant to the following description; it is only essential that a cut surface is generated in the cornea 17 of the eye 2.

Now, in order to perform an ophthalmic correction of refraction, a corneal volume is removed from a region within the cornea 17 by means of the laser radiation 6, separating tissue layers therein which isolate the corneal volume and enable the removal of the latter then. For isolation of the corneal volume to be removed, the position of the focus 17 of the focused laser radiation 7 in the cornea 17 is shifted, for example in cases where pulsed laser radiation is introduced. This is schematically shown in FIG. 3. The refractive properties of the cornea 17 are selectively modified by removal of the volume so as to achieve the correction of refraction. Therefore, said volume is lenticular in most cases and is referred to as a lenticle. The removal of the corneal volume is effected here as a re-treatment. It was either preceded by an ophthalmic correction of refraction, which left a residual need for correction, or is even an ophthalmic correction of refraction terminated during the operation, wherein the cut surfaces were generated incompletely. Of course, this also creates a need for correction.

FIG. 3 shows the elements of the treatment apparatus 1 only insofar as they are required in order to understand how the cut surfaces are produced. As already mentioned, the laser beam 6 is bundled in a focus 19 in the cornea 17, and the position of the focus 19 in the cornea is shifted such that focused energy from laser radiation pulses is introduced into the tissue of the cornea 17 at different locations so as to produce cut surfaces. The laser radiation 6 is preferably provided as pulsed radiation by the laser source 5. The scanner 8 has a two-part design in the construction of FIG. 3 and consists of an xy-scanner 8a, which is realized, in one variant, by two galvanometer mirrors with substantially orthogonal deflection. The scanner 8a two-dimensionally deflects the laser beam 6 coming from the laser source 5, so that a deflected laser beam 20 is present downstream of the scanner 8. Thus, the scanner 8a causes shifting of the position of the focus 19 substantially perpendicular to the main direction of incidence of the laser beam 6 in the cornea 17. For shifting of the depth position, a z-scanner 8b, preferably in the form of an adjustable telescope, for example, is provided in addition to the xy-scanner 8a in the scanner 8. The z-scanner 8b ensures that the z-position of the focus 19, i.e. its position along the optical axis of incidence, is changed. The z-scanner 8b may be arranged preceding or following the xy-scanner 8a.

It is not essential for the functional principle of the treatment apparatus 1 how the individual coordinates are assigned to the spatial directions nor that deflection by the scanner 8a is effected along mutually orthogonal axes. On the contrary, any scanner may be used which can shift the focus 19 in a plane in which the axis of incidence of the optical radiation is not located. Further, any non-Cartesian coordinate systems whatsoever can be used for deflection or control of the position of the focus 19. Examples include spherical coordinates or cylindrical coordinates.

The position of the focus 19 is controlled by the scanners 8a, 8b under the control of the control device 11, which performs suitable settings of the laser source 5, of the modulator 9 (not shown in FIG. 3) as well as of the scanner 8. The control device 11 ensures suitable operation of the laser source 5 as well as the three-dimensional focus shift described here as an example, thus finally producing a cut surface which isolates a determined corneal volume that is to be removed for correction of refraction.

The control device 11 works according to predetermined control data, which are predefined, for example, in the laser device 4 described here merely as an example, as target points for focus shifting. The control data are usually compiled in a control dataset, which provides geometrical parameters for the cut surface to be formed, e.g. the coordinates of the target points as a pattern. In this embodiment, the control dataset then also includes concrete set values for the focus position shifting mechanism, e.g. for the scanner 8.

FIG. 4 shows an example of how to produce the cut surface using the treatment apparatus 1. A corneal volume 21 is isolated in the cornea 17 by shifting the focus 19, into which the focused beam 7 is bundled. For this purpose, cut surfaces are formed, which are provided here, by way of example, as an anterior flap cut surface 22 as well as a posterior lenticle cut surface 23. These terms are to be understood here merely as examples and are intended to establish a relation to the conventional LASIK or FLEX methods, for which the treatment apparatus 1 is provided, as already described. It is only essential here that the cut surfaces 22 and 23 as well as peripheral cuts, which are not referred to in detail and which make the cut surfaces 22 and 23 converge at their peripheries, isolate the corneal volume 21. By means of an opening cut 24, a corneal lamella anteriorly limiting the corneal volume 21 can further be folded aside so as to allow removal of the corneal volume 21.

Figure 6:
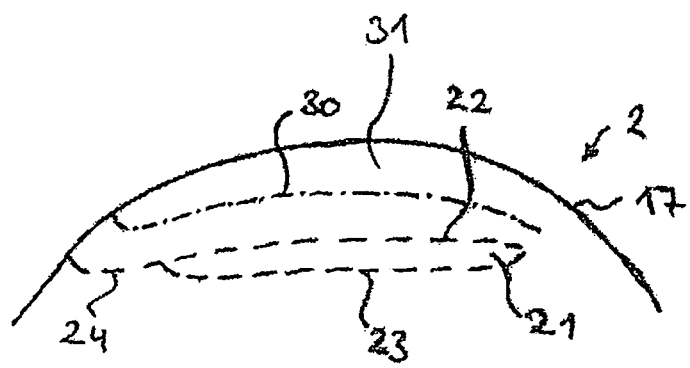
FIG. 6 shows a schematic sectional view of the cornea in connection with the ophthalmic correction of refraction in a re-treatment for correction of a residual eyesight defect.

FIG. 5 schematically shows the treatment apparatus 1, by reference to which the planning device 16 shall be explained in more detail. In this variant, the treatment apparatus 1 comprises at least two devices or modules. The laser device 4 already described emits the laser beam 6 onto the eye 2. As already described, operation of the laser device 4 is effected fully automatically by the control device 11, i.e., the laser device 4 starts generating and deflecting the laser beam 6 in response to a corresponding start signal and, thus, generates cut surfaces, which are structured as described, in order to remove the corneal volume 21. The laser device 5 receives the control signals required for operation from the control device 11, to which corresponding control data have been provided before. This is effected by the planning device 16, which is shown in FIG. 6 merely by way of example, as part of the control device 11. Of course, the planning device 16 may also be provided separately and may communicate with the control device 11 either in a wire-bound or wireless manner. It is then only essential to provide a corresponding data transmission channel between the planning device 16 and the control device 11.

The planning device 16 generates a control dataset which is provided to the control device 11 to carry out the ophthalmic correction of refraction. In doing so, the planning device uses measurement data relating to the cornea of the eye. In the presently described embodiment, these data come from a measurement device 28, which has previously measured the eye 2 of the patient 2. Of course, the measurement device 28 may have any design whatsoever and may transmit the corresponding data to the interface 29 of the planning device 16.

Now, the planning device assists the user of the treatment apparatus 1 in defining the cut surface for isolation of the corneal volume 21. This may even include a fully automatic definition of the cut surfaces, which may be effected, for example, by the planning device 16 using the measurement data to determine the corneal volume 21 to be removed, whose boundary surfaces are defined as cut surfaces, and generating therefrom suitable control data for the control device 11. At the other end of the degree of automation, the planning device 16 may provide input means by which a user inputs the cut surfaces in the form of geometrical parameters, etc. Intermediate steps provide suggestions for the cut surfaces, which the planning device 16 generates automatically and which can then be modified by an operator. Basically, all the concepts already explained in the above, more generic part of the description, can be applied here in the planning device 16.

In order to perform a re-treatment, the planning device 16 generates control data for cut surface production, which are then used in the treatment apparatus 1. FIG. 6 shows an example of the possible location of the cut surfaces, wherein the cut surfaces corresponding to those of FIG. 4 bear the same reference symbols. Now, the essential difference to the situation of FIG. 4 is that there already is an older cut 30 in the cornea 17, which cut resulted from a previous operation, e.g.

from an operation according to the FLEX method. In FIG. 6 as well as in the subsequent figures, the older cut 30 is indicated by a dot and dash line. For distinction from the older cut 30, the cut surfaces intended for re-treatment are indicated by a dashed line.

As FIG. 6 shows, the control data are defined such that the re-treatment cut surfaces eliminating the residual need for correction are all located beneath the older cut 30. Thus, with respect to the older cut 30, the corneal volume 21 to be removed is generated posteriorly, for example by a lenticle cut 23 and by a flap cut 22, including a lateral opening cut 24. This avoids any undesired interference with the older cut 30.

In a modification (not shown) of the cut surfaces of FIG. 6, all the cut surfaces provided or used for re-treatment may also be located within the corneal lamella 31 which has been generated between the older cut 30 and the anterior surface of the cornea 17.

Figure 7:
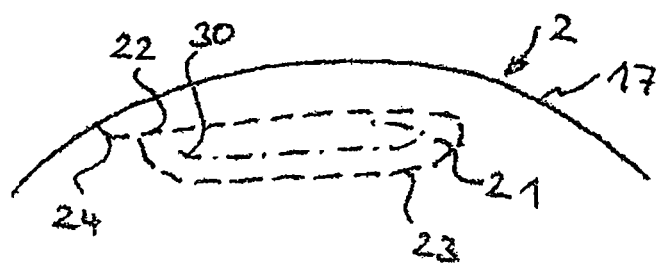
FIG. 7 shows a schematic sectional view of the cornea in connection with the ophthalmic correction of refraction in a re-treatment for continuation of a terminated previous operation.

FIG. 7 shows a further variant which is applicable, in particular, if there is no sufficiently exact knowledge about the extent to which the older cuts were carried out. The re-treatment cut surface, e.g. comprising a lenticle cut 23 and a flap cut 22, is now defined such that the older cuts 30 (again indicated by a dot and dash line) are located completely within the corneal volume 21 being removed for correction. This approach has the advantage that the number of boundary surfaces remaining in the cornea after the operation is small.

FIG. 8 shows a possibility which is applicable, in particular, if the positions of the older cuts are particularly well known. The re-treatment cut surfaces are then provided as continuations of the older cut 30. This is applicable, of course, where the previous operation was unintentionally terminated.

A further method of using older cuts is shown in FIG. 9, wherein the corneal volume 21 to be isolated is defined by both older cuts 30 and cut surfaces produced during re-treatment. As an example, the use of the older cut 30 as a flap cut is shown here, which is supplemented by a lenticle cut 23 generated in the re-treatment. This is to be understood as an example, of course, and it is also possible to use a cut extending into the lamella 31 as a supplement in the re-treatment.

In addition, it should also be noted that the treatment apparatus 1 or the planning device 16, respectively, also specifically realizes the method which was generally explained above.

A further embodiment of the planning device exists in the form of a computer program or of a corresponding data carrier comprising a computer program and realizing the planning device on a suitable computer so that the measurement data or the transplantation material data are input to the computer by suitable data transmission means and the control data are transmitted from this computer to the control device 11, for which purpose data transmission means known to the person skilled in the art are, in turn, suitable.

The invention claimed is:

1. A method of refraction-correcting ophthalmic surgery, said method comprising:
    accessing corneal data including information on pre-operative cuts generated in a previous ophthalmic operation;
    defining a corneal cut surface to thereby confine a corneal volume to be removed for refractive correction on the basis of the corneal data;
    generating a control dataset for the corneal cut surface;
    transmitting the control data to a treatment apparatus that comprises a laser device; and
    generating the cut surface by controlling the laser device using the control dataset.

2. The method as claimed in claim 1, further comprising emitting femtosecond pulse radiation from the laser device to isolate said corneal volume.

3. The method as claimed in claim 2, wherein the corneal cut surface continues the generated, pre-operative cuts.

4. The method of claim 3, wherein the corneal data are generated on the basis of a measurement of the eye, using a refractometer, a keratometer, an abberometer, or a wave-front measurement device.

5. The method of claim 3, wherein the cornea and the generated pre-operative cuts are simultaneously displayed.

6. The method of claim 2, wherein a course of the cut generation is logged.

* * * * *